United States Patent
Binder et al.

(10) Patent No.: US 6,942,990 B2
(45) Date of Patent: Sep. 13, 2005

(54) **GLUTARYL CEPHALOSPORIN AMIDASE FROM *PSEUDOMONAS DIMINUTA* BS-203**

(75) Inventors: Ross Binder, Manlius, NY (US); Joanne L. Brown, Dewitt, NY (US); Thomas J. Franceschini, Cicero, NY (US); William V. Burnett, Fayetteville, NY (US); Michael Politino, Syracuse, NY (US); Suo Win Liu, Manlius, NY (US); Sean M. Tonzi, Skaneateles, NY (US)

(73) Assignee: Bristol Myers Squibb Company, Princeton, NJ (US)

( * ) Notice: Subject to any disclaimer, the term of this patent is extended or adjusted under 35 U.S.C. 154(b) by 56 days.

(21) Appl. No.: 10/346,662

(22) Filed: Jan. 17, 2003

(65) Prior Publication Data

US 2003/0143715 A1 Jul. 31, 2003

Related U.S. Application Data

(62) Division of application No. 09/957,960, filed on Sep. 21, 2001, now Pat. No. 6,528,300.
(60) Provisional application No. 60/234,532, filed on Sep. 22, 2000.

(51) Int. Cl.$^7$ .......................... C12P 35/04; C12N 1/20; A01N 43/20
(52) U.S. Cl. ..................... 435/50; 435/253.3; 435/228; 514/43
(58) Field of Search ............................... 435/50, 253.3, 435/228; 514/43

(56) References Cited

U.S. PATENT DOCUMENTS

| | | |
|---|---|---|
| 3,960,662 A | 6/1976 | Matsuda et al. |
| 4,745,061 A | 5/1988 | Aretz et al. |
| 4,774,179 A | 9/1988 | Ichikawa et al. |
| 4,981,789 A | 1/1991 | Lein |
| 5,104,800 A | 4/1992 | Crawford et al. |
| 5,192,678 A | 3/1993 | Iwami et al. |
| 5,229,274 A | 7/1993 | Crawford et al. |
| 5,310,659 A | 5/1994 | Aramori et al. |
| 5,320,948 A | 6/1994 | Iwami et al. |
| 5,424,196 A | 6/1995 | Cambiaghi et al. |
| 5,618,687 A | 4/1997 | Wong et al. |
| 5,766,871 A | 6/1998 | Chu et al. |

FOREIGN PATENT DOCUMENTS

| | | |
|---|---|---|
| EP | 322032 | 6/1989 |
| EP | 405846 | 1/1991 |
| EP | 283218 | 7/1993 |
| EP | 482844 | 1/1996 |
| EP | 475652 | 3/1996 |
| EP | 525861 | 10/1996 |
| EP | 469919 | 4/1997 |

OTHER PUBLICATIONS

Matsuda et al Nucleotide sequences of the genes for two distinct cephalosporin acylases from a *Pseudomonas* strain. J Bacteriol. Dec. 1987;169(12):5821–6.*
Witkowski et al Conversion of a beta–ketoacyl synthase to a malonyl decarboxylase by replacement of the active–site cysteine with glutamine. Biochemistry. Sep. 7, 1999;38(36):11643–50.*
Whisstock et al Prediction of protein function from protein sequence and structure. Q Rev Biophys. Aug. 2003;36(3):307–40.*
Aramori et al., J. Bacteriol., vol. 173, pp. 7848–7855 (1991).
Matsuda et al., J. Bacteriol., vol. 169, pp. 5815–5820 (1987).
Ishiye et al., Biochim. Biophys. Acta., vol. 1132, pp. 233–239 (1992).
Honda et al., Biosci. Biotechnol. Biochem, vol. 61, pp. 948–955 (1997).
Matsuda et al., Journal of Bacteriology, vol. 169, No. 12, pp. 5821–5826 (1987).
Schumacher et al., Nucleic Acids Research, vol. 14, No. 14, pp. 5713–5727 (1986).
Stolp et al., The Prokaryotes, Chapter 61, pp. 719–741.
Kim et al., Biotechnology Letters, vol. 23, pp. 1067–1071 (2001).
Kim et al., J. Microbiol. Biotechnol., vol. 11, No. 3, pp. 452–457 (2001).

* cited by examiner

*Primary Examiner*—Rebecca E. Prouty
*Assistant Examiner*—Sheridan Swope
(74) *Attorney, Agent, or Firm*—Keith R. Lange

(57) ABSTRACT

The invention provides a glutaryl 7-ACA amidase from *Pseudomonas diminuta* strain BS-203, which catalyzes the hydrolysis of 7-β-(4-carboxybutanamido)-cephalosporanic acid to 7-aminocephalosporanic acid and glutaric acid. The invention also provides nucleic acid sequences, vectors, and host cells useful in the production of this amidase. The glutaryl 7-ACA amidase can be used for the preparation of 7-aminocephalosporanic acid.

21 Claims, 5 Drawing Sheets

```
Leu Val Met Gly Asp Tyr Ala Glu Ser Leu          (SEQ ID NO:3)
    Val Met Gly Asp Tyr Ala

5'-GTX ATG GGX GAY TAY GC-3'                     (SEQ ID NO:4)
5'-GC RTA RTC XCC CAT XAC-3'                     (SEQ ID NO:5)

5'-GC ATA ATC ACC CAT XAC-3'                     (SEQ ID NO:6)
5'-GC ATA ATC CCC CAT XAC-3'                     (SEQ ID NO:7)
5'-GC ATA ATC GCC CAT XAC-3'                     (SEQ ID NO:8)
5'-GC ATA ATC TCC CAT XAC-3'                     (SEQ ID NO:9)
5'-GC ATA GTC ACC CAT XAC-3'                     (SEQ ID NO:10)
5'-GC ATA GTC CCC CAT XAC-3'                     (SEQ ID NO:11)
5'-GC ATA GTC GCC CAT XAC-3'                     (SEQ ID NO:12)
5'-GC ATA GTC TCC CAT XAC-3'                     (SEQ ID NO:13)
5'-GC GTA ATC ACC CAT XAC-3'                     (SEQ ID NO:14)
5'-GC GTA ATC CCC CAT XAC-3'                     (SEQ ID NO:15)
5'-GC GTA ATC GCC CAT XAC-3'                     (SEQ ID NO:16)
5'-GC GTA ATC TCC CAT XAC-3'                     (SEQ ID NO:17)
5'-GC GTA GTC ACC CAT XAC-3'                     (SEQ ID NO:18)
5'-GC GTA GTC CCC CAT XAC-3'                     (SEQ ID NO:19)
5'-GC GTA GTC GCC CAT XAC-3'                     (SEQ ID NO:20)
5'-GC GTA GTC TCC CAT XAC-3'                     (SEQ ID NO:21)
```

Figure 2

```
Fragment: Gly Phe Ala Val Thr His Tyr Leu Ser Gly Ala Ile Gly Glu Ala-
Probe: 5'-GGT TTT GCT GTC ACG CAT TAT CTC AGT GGT GCT ATT GGT GAG GCT- Ala Gly Glu Leu Ser Gln Asp Ala Glu Ile Ala Arg
          GCT GGT GAG CTC AGT CAG GAT GCT GAG ATT GC-3'    (SEQ ID NO:22
```

Figure 3

```
   1  GGTCTCGGTC GGAATACGGT GTGATGCCGG CGATGCCGTC TTGGCCGATG AGAGCGCGTC
  61  ATCGTTCTGT CACCCGACGA AGTCGCTGCG GAAGCACAGA AGGCCATCGA AACGCAGATC
 121  CGCGGCAAGG CCCGCGAAGC CAGCGTTCGC GAGACCGGCG TCAAGCTTGG TGACCTGTCG
 181  GGTGCAACCG CCAAGGTTCT GGCAAAGCTC GGCTGATCGA TACCCTCTAG CCGGAGCATC
                                                          start ↓ (293)
 241  GTGCCCCGGC TAGTCTCCCC CGACTGCCTT ACCCATCGAA TTGAGATCCG ACATGACCCG
 301  TCCAAGCCTG CCGTTCACCT GCGAGAAATC CCCGGCCAGC GGTGCCGGCG CATGGTGGT
 361  GACCAACCAT CCTCTGGGCT CGGCGGCCGG GTTCGAGATA CTGGCGGCGG GCGGCAATGC
 421  GGTGGATGCC GCGGTTGCCT CGCTGCTGGC ATTGACCGTG GTCGAGCCGA TGATGGTCGG
 481  CATTGCCGGT GGCGGGCTGT CGCATCTGCG GATGGCTGAC GGAACGCATG TGGTTGATCG
 541  ACGCCCTGTT CTTCCGCCGC AGCGACCATG CATCCGGAAA TCTACGAACC GGTTTCCGAC
 601  GAACCGGCTC GCTACATGGA CGCCAAGGGG CGTCGCAATA TTCATCGGAG CATCCTCGGT
 661  CGCGGTCCCC GGCAACCTGG CCGGCTGGTG CGACATGCAG GCACTTTACG CAAGCTGCC
 721  CTTTGCCGAC ATTGTCGAGC CGGCGATCCG GCTGGCCTCG CGCGGCTTTG CCGTCACCCA
 781  TTATCTGTCC GGCGCCATTG GCGAGGCCGC CGGCGAGCTT TCGCAGGATG CGGAAATCGC
 841  CAGAATTCTC ATGCCCGGCG GTGCGGCCCC GGCTCCGGGC GATCGCCTCG TGATGGGCGA
 901  TTATGCCGAG AGCCTGCGGC TGATCCAGCG CGAAGGGGCA GCAGCTCTGC ATGGTGGCGC
 961  CCTTGGCGCC GCACTCGCCG CAAGAATGTT GACGGGCGG GACGATGCGG GCTGGGTCAC
1021  CGAAGCCGAC TTGCGCGCCT ACCGGCCGAT CGAGCGCAAA CCGATCATCG GTAACTATCG
1081  CGGTTTCGAA GATTGCCGGA CACACACGGC TTCTTCCGGC GTGCATGTCA CCCAGATGCT
1141  CAACATGCTG GAAGCCTATG ACGTGGGCAT GGGCTTCGGC AGTCCCGCAT CGCTGCATCT
1201  TCTGGCAGAA GTGATCCGCA TCGCGTTTGC CGACCGTCGC GCCTATTCGG GCGATCCGGC
1261  CTTTGTCGAC GTGCCGGTCG AAAGGTTGAC CTCCAAGGCC TATGCCGAGG AATGCCGCGC
1321  CCAGATCCGC CGGGCTGCCA GCCTGCCGGC ACCGCGGGCA CCGGGTTATG AAAGCCACGA
1381  CACGACCCAC ATAACGGTTG CCGACGGGAT GGCAACATTG TACACGGCCA CGCATACGAT
1441  CAACGGACTT TTCGGCGCAC GCCTGGCCGT GCCGGGTACC GGATTCATCC CCAACAACTA
1501  TATGAGCAAT TTCGACCCGC ATCCCGGCAA TGCCTTGTCG GTGGTTCCGG GCAAGCGGGT
1561  GCCGACCTCG ATGGCGCCGA TGATCCTGAT GAAGGATGGC GCCCCGGTAT TCGCGCTTGG
1621  CCTGCCTGGC GGCTTGCGCA TTTTCCCCTC GGCCATGCAA GCGATCGTCA ATCTGATCGA
1681  CCACAAGATG AGCCTGCAGG AAGCGGTGGA AGCGCCGCGT ATCTGGACAC AAGGCCAGGA
1741  AGTGGAAATC GAGCAGGCCT ACGCACAGCA ACAGCAAAAG CTCGAAGAAC TCGGTCACGA
1801  AGGTCGGGTG ATGCCGCATA TCGGTGGCGG CATGAATGCC ATCGCATTCG GTGACACCAT
1861  GACCGGCGCC GCATGCTGGC GTGCCGATGG CACCGTGGCT GCACTCGGCG GAGGATTGGC
1921  GCGCCCGGGC GTCCGGTTCT GGCCAGACAA GGCACCTGCC CAAGCCCGCA TAGGGCAGGG
                stop↓ (1993)
1981  GAGTTTGAGC ACATAAAAGA CGCATGCCGC CGGCAGTCGC GGTAATGCTG GCTGCTCAGC
2041  ACCATATCTC CATGAATTGC AATCGAAGAC GACGTTCAGA AGTTTTATGC CTCTGGCATC
2101  CGGAGAAGGC CACCAATGAA CACAAGGTTC ACTGCTCTTG ACGGGTGCCA GCCGGGGTAT
2161  AGGCCACGCA CGGTCAAACT GTTTTTGGAG 2190               (SEQ ID NO:1)
```

Figure 4

```
  1 MTRPSLPFTC EKSPASGAGG MVVTNHPLGS AAGFEILAAG GNAVDAAVAS LLALTVVEPM
 61 MVGIAGGGLS HLRMADGTHV VDRRPVLPPQ RPCIRKSTNR FPTNRLATWT PRGVAIFIGA
121 SSVAVPGNLA GWCDMQALYG KLPFADIVEP AIRLASRGFA VTHYLSGAIG EAAGELSQDA
181 EIARILMPGG AAPAPGDRLV MGDYAESLRL IQREGAAALH GGALGAALAA RMLTGGDDAG
241 WVTEADLRAY RPIERKPIIG NYRGFEDCRT HTASSGVHVT QMLNMLEAYD VGMGFGSPAS
301 LHLLAEVIRI AFADRRAYSG DPAFVDVPVE RLTSKAYAEE CRAQIRRAAS LPAPRAPGYE
       ↓ (putative cleavage site)
361 SHDTTHITVA DGMATLYTAT HTINGLFGAR LAVPGTGFIP NNYMSNFDPH PGNALSVVPG
421 KRVPTSMAPM ILMKDGAPVF ALGLPGGLRI FPSAMQAIVN LIDHKMSLQE AVEAPRIWTQ
481 GQEVEIEQAY AQQQQKLEEL GHEGRVMPHI GGGMNAIAFG DTMTGAACWR ADGTVAALGG
541 GLARPGVRFW PDKAPAQARI GQGSLST 567           (SEQ ID NO:2)
```

Figure 5

SEQUENCE LISTING

```
<160> NUMBER OF SEQ ID NOS: 25
<210> SEQ ID NO 1
<211> LENGTH: 2190
<212> TYPE: DNA
<213> ORGANISM: Pseudomonas diminuta

<400> SEQUENCE: 1
ggtctcggtc ggaatacggt gtgatgccgg cgatgccgtc ttggccgatg agagcgcgtc     60
atcgttctgt cacccgacga agtcgctgcg gaagcacaga aggccatcga aacgcagatc    120
cgcggcaagg cccgcgaagc cagcgttcgc gagaccggcg tcaagcttgg tgacctgtcg    180
ggtgcaaccg ccaaggttct ggcaaagctc ggctgatcga taccctctag ccggagcatc    240
gtgccccggc tagtctcccc cgactgcctt acccatcgaa ttgagatccg acatgacccg    300
tccaagcctg ccgttcacct gcgagaaatc cccgccagc ggtgccggcg gcatggtggt    360
gaccaaccat cctctgggct cggcggccgg gttcgagata ctggcggcgg gcggcaatgc    420
```

```
ggtggatgcc gcggttgcct cgctgctggc attgaccgtg gtcgagccga tgatggtcgg      480
cattgccggt ggcgggctgt cgcatctgcg gatggctgac ggaacgcatg tggttgatcg      540
acgccctgtt cttccgccgc agcgaccatg catccggaaa tctacgaacc ggtttccgac      600
gaaccggctc gctacatgga cgccaagggg cgtcgcaata ttcatcggag catcctcggt      660
cgcggtcccc ggcaacctgg ccggctggtg cgacatgcag gcactttacg caagctgcc       720 ctttgccgac attgtcgagc cggcgatccg gctggcctcg cgcggctttg ccgtcaccca      780
ttatctgtcc ggcgccattg gcgaggccgc cggcgagctt cgcaggatgc ggaaatcgc       840 cagaattctc atgcccggcg gtgcggcccc ggctccgggc gatcgcctcg tgatgggcga      900
ttatgccgag agcctgcggc tgatccagcg cgaaggggca gcagctctgc atggtggcgc      960
ccttggcgcc gcactcgccg caagaatgtt gacgggcggc gacgatgcgg gctgggtcac     1020
cgaagccgac ttgcgcgcct accggccgat cgagcgcaaa ccgatcatcg gtaactatcg     1080
cggtttcgaa gattgccgga cacacacggc ttcttccggc gtgcatgtca cccagatgct     1140
caacatgctg gaagcctatg acgtgggcat gggcttcggc agtcccgcat cgctgcatct     1200
tctggcagaa gtgatccgca tcgcgtttgc cgaccgtcgc gcctattcgg gcgatccggc     1260 cttttgtcgac gtgccggtcg aaaggttgac ctccaaggcc tatgccgagg aatgccgcgc     1320
ccagatccgc cgggctgcca gcctgccggc accgcgggca ccgggttatg aaagccacga     1380
cacgacccac ataacggttg ccgacgggat ggcaacattg tacacggcca cgcatacgat     1440
caacggactt tcggcgcac gcctggccgt gccgggtacc ggattcatcc ccaacaacta     1500
tatgagcaat ttcgacccgc atccggcaa tgccttgtcg gtggttccgg gcaagcgggt     1560
gccgacctcg atggcgccga tgatcctgat gaaggatggc gccccggtat cgcgcttgg     1620 cctgcctggc ggcttgcgca ttttcccctc ggccatgcaa gcgatcgtca atctgatcga     1680
ccacaagatg agcctgcagg aagcggtgga agcgccgcgt atctggacac aaggccagga     1740
agtgaaaatc gagcaggcct acgcacagca acagcaaaag ctcgaagaac tcggtcacga     1800
aggtcgggtg atgccgcata tcggtggcgg catgaatgcc atcgcattcg gtgacaccat     1860
gaccggcgcc gcatgctggc gtgccgatgg caccgtggct gcactcggcg gaggattggc     1920
gcgcccgggc gtccggttct ggccagacaa ggcacctgcc caagcccgca tagggcaggg     1980
gagtttgagc acataaaaga cgcatgccgc cggcagtcgc ggtaatgctg gctgctcagc     2040
accatatctc catgaattgc aatcgaagac gacgttcaga agtttttatgc ctctggcatc     2100 cggagaaggc caccaatgaa cacaaggttc actgctcttg acgggtgcca gccggggtat     2160
aggccacgca cggtcaaact gttttttggag                                      2190
```

<210> SEQ ID NO 2
<211> LENGTH: 567
<212> TYPE: PRT
<213> ORGANISM: Pseudomonas diminuta

<400> SEQUENCE: 2

```
Met Thr Arg Pro Ser Leu Pro Phe Thr Cys Glu Lys Ser Pro Ala Ser
1               5                  10                  15

Gly Ala Gly Gly Met Val Val Thr Asn His Pro Leu Gly Ser Ala Ala
            20                  25                  30

Gly Phe Glu Ile Leu Ala Ala Gly Gly Asn Ala Val Asp Ala Ala Val
        35                  40                  45

Ala Ser Leu Leu Ala Leu Thr Val Val Glu Pro Met Met Val Gly Ile
```

-continued

```
              50                  55                  60
Ala Gly Gly Leu Ser His Leu Arg Met Ala Asp Gly Thr His Val
65                  70                  75                  80

Val Asp Arg Arg Pro Val Leu Pro Pro Gln Arg Pro Cys Ile Arg Lys
                85                  90                  95

Ser Thr Asn Arg Phe Pro Thr Asn Arg Leu Ala Thr Trp Thr Pro Arg
                100                 105                 110

Gly Val Ala Ile Phe Ile Gly Ala Ser Val Ala Val Pro Gly Asn
                115                 120                 125

Leu Ala Gly Trp Cys Asp Met Gln Ala Leu Tyr Gly Lys Leu Pro Phe
130                 135                 140

Ala Asp Ile Val Glu Pro Ala Ile Arg Leu Ala Ser Arg Gly Phe Ala
145                 150                 155                 160

Val Thr His Tyr Leu Ser Gly Ala Ile Gly Glu Ala Ala Gly Glu Leu
                165                 170                 175

Ser Gln Asp Ala Glu Ile Ala Arg Ile Leu Met Pro Gly Gly Ala Ala
                180                 185                 190

Pro Ala Pro Gly Asp Arg Leu Val Met Gly Asp Tyr Ala Glu Ser Leu
                195                 200                 205

Arg Leu Ile Gln Arg Glu Gly Ala Ala Leu His Gly Gly Ala Leu
210                 215                 220

Gly Ala Ala Leu Ala Ala Arg Met Leu Thr Gly Gly Asp Asp Ala Gly
225                 230                 235                 240

Trp Val Thr Glu Ala Asp Leu Arg Ala Tyr Arg Pro Ile Glu Arg Lys
                245                 250                 255

Pro Ile Ile Gly Asn Tyr Arg Gly Phe Glu Asp Cys Arg Thr His Thr
                260                 265                 270

Ala Ser Ser Gly Val His Val Thr Gln Met Leu Asn Met Leu Glu Ala
                275                 280                 285

Tyr Asp Val Gly Met Gly Phe Gly Ser Pro Ala Ser Leu His Leu Leu
                290                 295                 300

Ala Glu Val Ile Arg Ile Ala Phe Ala Asp Arg Arg Ala Tyr Ser Gly
305                 310                 315                 320

Asp Pro Ala Phe Val Asp Val Pro Val Glu Arg Leu Thr Ser Lys Ala
                325                 330                 335

Tyr Ala Glu Glu Cys Arg Ala Gln Ile Arg Arg Ala Ala Ser Leu Pro
                340                 345                 350

Ala Pro Arg Ala Pro Gly Tyr Glu Ser His Asp Thr Thr His Ile Thr
                355                 360                 365

Val Ala Asp Gly Met Ala Thr Leu Tyr Thr Ala Thr His Thr Ile Asn
                370                 375                 380

Gly Leu Phe Gly Ala Arg Leu Ala Val Pro Gly Thr Gly Phe Ile Pro
385                 390                 395                 400

Asn Asn Tyr Met Ser Asn Phe Asp Pro His Pro Gly Asn Ala Leu Ser
                405                 410                 415

Val Val Pro Gly Lys Arg Val Pro Thr Ser Met Ala Pro Met Ile Leu
                420                 425                 430

Met Lys Asp Gly Ala Pro Val Phe Ala Leu Gly Leu Pro Gly Gly Leu
                435                 440                 445

Arg Ile Phe Pro Ser Ala Met Gln Ala Ile Val Asn Leu Ile Asp His
                450                 455                 460

Lys Met Ser Leu Gln Glu Ala Val Glu Ala Pro Arg Ile Trp Thr Gln
465                 470                 475                 480
```

-continued

Gly Gln Glu Val Glu Ile Glu Gln Ala Tyr Ala Gln Gln Gln Lys
              485                 490                 495

Leu Glu Leu Gly His Glu Gly Arg Val Met Pro His Ile Gly Gly
              500                 505                 510

Gly Met Asn Ala Ile Ala Phe Gly Asp Thr Met Thr Gly Ala Ala Cys
              515                 520                 525

Trp Arg Ala Asp Gly Thr Val Ala Ala Leu Gly Gly Leu Ala Arg
          530                 535                 540

Pro Gly Val Arg Phe Trp Pro Asp Lys Ala Pro Ala Gln Ala Arg Ile
545                 550                 555                 560

Gly Gln Gly Ser Leu Ser Thr
              565

<210> SEQ ID NO 3
<211> LENGTH: 10
<212> TYPE: PRT
<213> ORGANISM: Pseudomonas diminuta

<400> SEQUENCE: 3

Leu Val Met Gly Asp Tyr Ala Glu Ser Leu
1               5                   10

<210> SEQ ID NO 4
<211> LENGTH: 17
<212> TYPE: DNA
<213> ORGANISM: Pseudomonas diminuta
<220> FEATURE:
<221> NAME/KEY: misc_feature
<222> LOCATION: (3)..(9)
<223> OTHER INFORMATION: n is a, g, c or t

<400> SEQUENCE: 4
gtnatgggng aytaygc                                                17

<210> SEQ ID NO 5
<211> LENGTH: 17
<212> TYPE: DNA
<213> ORGANISM: Pseudomonas diminuta
<220> FEATURE:
<221> NAME/KEY: misc_feature
<222> LOCATION: (9)..(15)
<223> OTHER INFORMATION: n is a, g, c or t

<400> SEQUENCE: 5
gcrtartcnc ccatnac                                                17

<210> SEQ ID NO 6
<211> LENGTH: 17
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 6
gcataatcac ccatnac                                                17

<210> SEQ ID NO 7
<211> LENGTH: 17
<212> TYPE: DNA
<213> ORGANISM: Artificial sequence

```
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 7
gcataatccc ccatnac                                                  17

<210> SEQ ID NO 8
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 8
gcataatcgc ccatnac                                                  17

<210> SEQ ID NO 9
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 9
gcataatctc ccatnac                                                  17

<210> SEQ ID NO 10
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 10
gcatagtcac ccatnac                                                  17

<210> SEQ ID NO 11
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 11
gcatagtccc ccatnac                                                  17

<210> SEQ ID NO 12
<211> LENGTH: 17
<212> TYPE: DNA
```

-continued

```
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 12
gcatagtcgc ccatnac                                                  17

<210> SEQ ID NO 13
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 13
gcatagtctc ccatnac                                                  17

<210> SEQ ID NO 14
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 14
gcgtaatcac ccatnac                                                  17

<210> SEQ ID NO 15
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c, or t

<400> SEQUENCE: 15
gcgtaatccc ccatnac                                                  17

<210> SEQ ID NO 16
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 16
gcgtaatcgc ccatnac                                                  17

<210> SEQ ID NO 17
<211> LENGTH: 17
```

```
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 17
gcgtagtcac ccatnac                                                      17

<210> SEQ ID NO 18
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 18
gcgtagtcac ccatnac                                                      17

<210> SEQ ID NO 19
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 19
gcgtagtccc ccatnac                                                      17

<210> SEQ ID NO 20
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 20
gcgtagtcgc ccatnac                                                      17

<210> SEQ ID NO 21
<211> LENGTH: 17
<212> TYPE: DNA
<213> ORGANISM: Artificial sequence
<220> FEATURE:
<223> OTHER INFORMATION: oligonucleotide probe
<220> FEATURE:
<221> NAME/KEY: misc_feature
<222> LOCATION: (15)..(15)
<223> OTHER INFORMATION: n is a, g, c or t

<400> SEQUENCE: 21
gcgtagtctc ccatnac                                                      17

<210> SEQ ID NO 22
```

-continued

```
<211> LENGTH: 77
<212> TYPE: DNA
<213> ORGANISM: Artificial sequence
<220> FEATURE:
<223> OTHER INFORMATION: oligonucleotide probe

<400> SEQUENCE: 22
ggttttgctg tcacgcatta tctcagtggt gctattggtg aggctgctgg tgagctcagt      60
caggatgctg agattgc                                                    77

<210> SEQ ID NO 23
<211> LENGTH: 17
<212> TYPE: DNA
<213> ORGANISM: Coliphage M13

<400> SEQUENCE: 23
gtaaaacgac ggccagt                                                    17

<210> SEQ ID NO 24
<211> LENGTH: 21
<212> TYPE: DNA
<213> ORGANISM: Pseudomonas diminuta

<400> SEQUENCE: 24
ttgagatccg acatgacccg t                                               21

<210> SEQ ID NO 25
<211> LENGTH: 21
<212> TYPE: DNA
<213> ORGANISM: Artificial sequence
<220> FEATURE:
<223> OTHER INFORMATION: oligonucleotide containing BspHI restriction
      enzyme site

<400> SEQUENCE: 25
ttgagatccg tcatgacccg t                                               21
```

GLUTARYL CEPHALOSPORIN AMIDASE FROM *PSEUDOMONAS DIMINUTA* BS-203

This application is a divisional of application Ser. No. 09/957,960, filed Sep. 21, 2001, which issued as U.S. Pat. No. 6,528,300 on Feb. 13, 2003, and which claims the benefit of provisional application 60/234,532, filed Sep. 22, 2000, which is incorporated herein by reference in its entirety.

rial for the synthesis of many semi-synthetic cephalosporin antibiotics. 7-ACA can be generated from cephalosporin C (a readily available fermentation product) by a two-step enzymatic process (Scheme 1), using first a D-amino acid oxidase in conjunction with oxidative decarboxylation to produce glutaryl 7-ACA (Step A), and then using a glutaryl 7-ACA acylase to remove the glutaryl group to produce 7-ACA (Step B).

Scheme 1

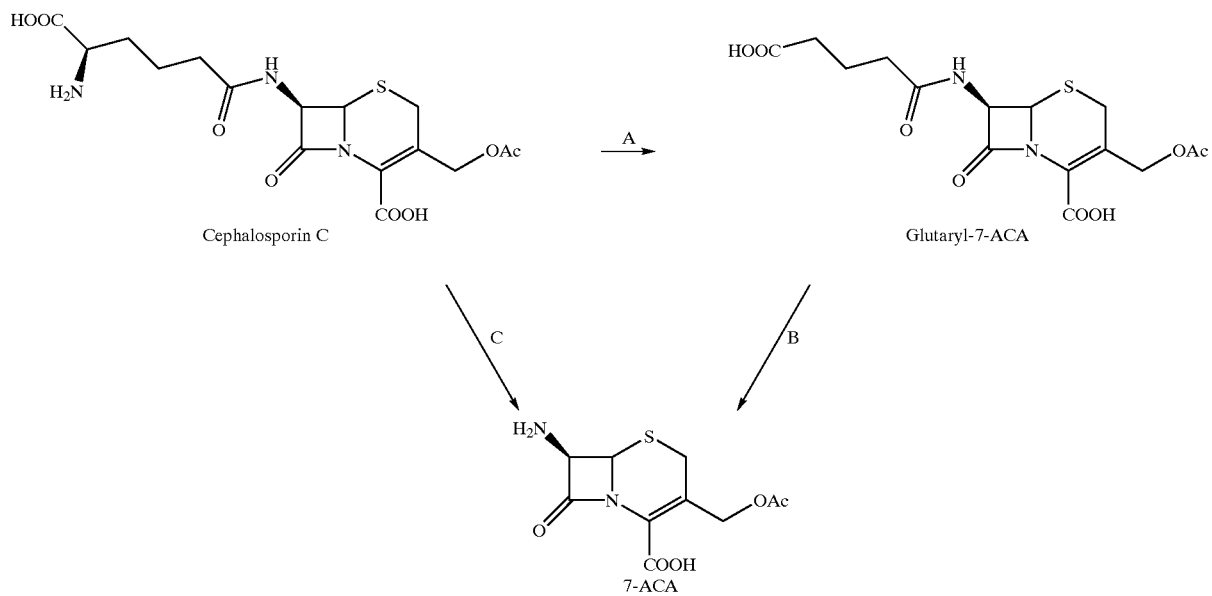

FIELD OF THE INVENTION

This invention relates to a novel glutaryl cephalosporin amidase (glutaryl 7-ACA amidase) enzyme from *Pseudomonas diminuta* BS-203, which catalyzes the hydrolysis of 7-(4-carboxybutanamido)-3-acetoxymethyl-3-cephem-4-carboxylic acid (glutaryl 7-ACA) to yield 7-aminocephalosporanic acid (7-ACA) and glutaric acid. The invention also relates to nucleic acids having sequences which encode the glutaryl 7-ACA enzyme, including the nucleic acid sequence of the glutaryl 7-ACA amidase gene from *P. diminuta* BS-203, and to nucleic acid sequences derived therefrom. The invention also relates to vectors and host cells containing these nucleic acid sequences, and methods of producing glutaryl 7-ACA amidase with these vectors and host cells. The invention also relates to a method of preparing 7-ACA by using glutaryl 7-ACA amidase from *P. diminuta* BS-203.

BACKGROUND OF THE INVENTION

3-Acetoxymethyl 7-amino-3-cephem-4-carboxylic acid (7-aminocephalosporanic acid, 7-ACA) is the starting mate- Steps A and B can also be carried out by chemical processes. The chemical processes, which involve the use of large quantities of organic solvents and toxic chemicals, have safety and environmental disadvantages. By using enzymatic processes, on the other hand, 7-ACA is obtained under mild conditions in an aqueous solvent system. Enzymes that catalyze the hydrolysis of glutaryl 7-ACA to 7-ACA (Step B) have been readily available, but enzymes that efficiently catalyze direct hydrolysis of cephalosporin C to 7-ACA (Step C) have not. Consequently, a two-step process has been generally employed, where step A is carried out chemically or enzymatically, and step B is carried out enzymatically. See for example Cambiaghi et al., U.S. Pat. No. 5,424,196, and references therein.

Step A is usually carried out with D-amino acid transaminases (also known as D-amino acid oxidase, EC-1.4.3.3) (Aretz et al., U.S. Pat. No. 4,745,061), in order to oxidize the amino group of the D-amino acid side chain to a keto group, followed by treatment with hydrogen peroxide to effect decarboxylation and provide glutaryl 7-ACA.

Much effort has gone into the development of efficient methods for carrying out Step B. Crawford et al., in U.S. Pat. No. 5,104,800, provide a brief summary of earlier work in the field of 7-ACA synthesis. Matsuda et al, in U.S. Pat. No. 3,960,662, describe glutaryl 7-ACA amidase activity from cultures of Comamonas sp. and *Pseudomonas ovalis*. Workers at Fujisawa Pharmaceutical Co. (Aramori et al., U.S. Pat. No. 5,310,659 and EP 0482844; Aramori et al., 1991, *J. Bacteriol.* 173:7848–7855) describe a glutaryl 7-ACA acylase isolated from *Bacillus (Brevibacillus) laterosporus*. Chu et al. (U.S. Pat. No. 5,766,871) describe a glutaryl 7-ACA acylase isolated from *Pseudomonas nitroreducens*. Battistel et al., in EP 0525861, describe glutaryl 7-ACA acylases from various *Pseudomonas, Bacillus*, and *Achromobacter* species.

A number of enzymes capable of directly catalyzing hydrolysis of cephalosporin C to 7-ACA (Scheme 1, Step C) have been reported. For example, workers at Asahi Chemical (Ichikawa et al., U.S. Pat. No. 4,774,179; Matsuda et al., *J. Bact.,* 1987, 169:5815–5820 and 5821–5826) disclosed strain SE-495 of *Pseudomonas diminuta*, and strain SE83 of a closely related *Pseudomonas* species, both of which produce enzymes capable of effecting the direct conversion of cephalosporin C into 7-ACA. Lein, in U.S. Pat. No. 4,981,789 and EP 0283218, reported a cephalosporin C amidase from *Arthrobacter viscous*. Lein, in EP 0322032, reported a cephalosporin C amidase from *Bacillus megaterium*, as did Crawford et al., in U.S. Pat. No. 5,104,800 (and divisional U.S. Pat. No. 5,229,247) and EP 0405846. Iwami et al., in U.S. Pat. No. 5,192,678 (and divisional U.S. Pat. No. 5,320,948) and EP 0475652 later disclosed a cephalosporin C acylase from *Pseudomonas diminuta* N-176 which is capable of carrying out Step C directly, but which is more adept at catalyzing the conversion of glutaryl 7-ACA into 7-ACA. Such enzymes have not yet been shown to be economically viable for production of 7-ACA.

Preparation of recombinant host cells expressing various glutaryl 7ACA amidases has been described by numerous workers. See for example M. Ishiye and M. Niwa, *Biochim. Biophys. Acta,* 1992, 1132:233–239; Croux et al., EP 0469919; Aramori et al., U.S. Pat. No. 5,310,659; Iwami et al., U.S. Pat. No. 5,192,678; and Honda et al., *Biosci. Biotechnol. Biochem.,* 1997, 61:948–955, all of which are incorporated herein by reference.

In view of the value of 7-ACA as a pharmaceutical intermediate, there exists a need for improved 7-ACA amidases that provide superior results in terms of factors such as enzyme cost, reaction rate and yield, and enzyme stability.

SUMMARY OF THE INVENTION

The invention provides a novel glutaryl 7-ACA amidase isolated from the bacterial strain *Pseudomonas diminuta* BS-203, and derivative, subunits, and fragments thereof. The invention also provides oligonucleotides, i.e. DNA and RNA molecules, comprising a nucleic acid sequence encoding the glutaryl 7-ACA amidase of the invention, as well as derivatives, fragments and partial sequences thereof, and polynucleotides complementary to the DNA molecules of the invention. The present invention also relates to vectors and host cells comprising the polynucleotides of the invention.

The invention also provides homologous proteins, preferably having at least 80% homology to the *Pseudomonas diminuta* BS-203 glutaryl 7-ACA amidase. Proteins having up to 113 conservative amino acid substitutions, and/or up to 20 amino acid additions or deletions, are contemplated as being part of the invention. Nucleic acid sequences encoding such homologous proteins are also contemplated as being part of the invention.

The invention further relates to methods of obtaining the *Pseudomonas diminuta* BS-203 amidase by culturing *P. diminuta* BS-203 in a suitable medium, and recovering a protein fraction having glutaryl 7-ACA arnidase activity. The invention also relates to methods of using the nucleic acids, vectors, and host cells of the invention to produce the glutaryl 7-ACA amidase of the invention.

The invention further relates to a process for obtaining 7-aminocephalosporanic acid (7-ACA) from 7-β-(4-carboxybutanamido)cephalosporanic acid (glutaryl 7-ACA) and other 7-β-(acylamido)cephalosporanic acids, by contacting such substrates with a glutaryl 7-ACA amidase of the invention. The invention also relates to a process for producing desacetyl 7-ACA, from the desacetyl derivatives of 7-β-(4-carboxybutanamido)cephalosporanic acid (glutaryl 7-ACA) and other 7-β-(acylamido)cephalosporanic acids, by contacting such substrates with a glutaryl 7-ACA amidase of the invention.

BRIEF DESCRIPTION OF THE FIGURES

FIG. 2 shows a sequence of 10 amino acids from the glutaryl 7-ACA amidase of *Pseudomonas diminuta* BS-203 (SEQ ID NO:3), a 6 amino acid subset of this sequence, a generic nucleotide sequence that could encode these six amino acids (SEQ ID NO:4), the complementary sequence (the generic complementary sequence; SEQ ID NO:5), and the nucleotide sequences of sixteen degenerate oligonucleotide probes (SEQ ID NOS: 6–21) corresponding to the generic complementary sequence. In the figure, X=A, C, G, or T; Y=C or T; R=A or G.

FIG. 3 shows a glutaryl 7-ACA amidase amino acid sequence (a portion of SEQ ID NO:2), and the nucleotide sequence of a 77-base pair "guess-mer" probe (SEQ ID NO:22) derived from it.

FIG. 4 shows the complete nucleotide sequence of the glutaryl 7-ACA amidase gene from *Pseudomonas diminuta* BS-203 (SEQ ID NO:1). Translation start and stop sites are indicated by arrows. Regions complementary to one of the degenerate probes (SEQ ID NO 8) and the guessmer probe (SEQ ID NO:22) are underlined.

FIG. 5 shows the complete amino acid sequence of the glutaryl 7-ACA amidase precursor protein from *Pseudomonas diminuta* BS-203 (SEQ ID NO: 2) encoded by the nucleotide sequence of FIG. 4. The arrow indicates the likely site of cleavage into subunits. Regions complementary to one of the degenerate probes (SEQ ID NO: 8) and the guessmer probe (SEQ ID NO:22) are underlined.

DETAILED DESCRIPTION OF THE INVENTION

Figure 1:
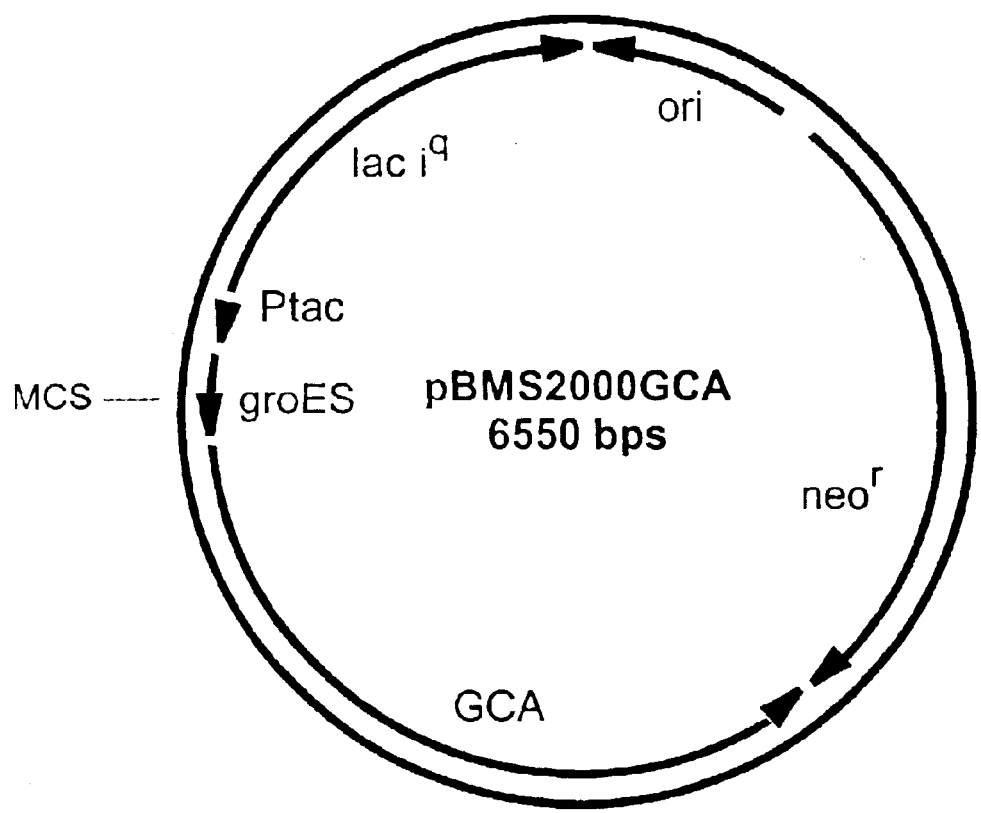
FIG. 1 shows the restriction map of the *E. coli* expression plasmid pBMS2000GCA. Abbreviations used are Ptac: tac transcriptional promoter groES: groES chaperone gene MCS: multiple cloning site ori: origin of DNA replication neo[r]: neomycin resistance gene lac i[q]: transcriptional repressor gene GCA: glutaryl 7-ACA amidase gene

The invention relates to the isolation and characterization of a novel glutaryl 7-ACA amidase. In particular, the invention relates to a glutaryl 7-ACA amidase produced by *Pseudomonas diminuta* BS-203 having the amino acid sequence shown in SEQ ID NO:2. The aligned sequence shows about 56% identity (320 matches) to the sequence of the "acyI" cephalosporin acylase from *Pseudomonas* sp. strain SE83 (Matsuda et al., *J. Bact.* 1987 169:5821–5826) and to the nearly identical enzyme isolated from *Pseudomonas* sp. strain V22 (M. Ishiye and M. Niwa, *Biochim.*

*Biophys. Acta,* 1992, 1132:233–239. Interestingly, there is only about 20% identity between the *P. diminuta* BS-203 enzyme of the present invention and the *P. diminuta* N-176 enzyme of Iwami et al. (U.S. Pat. No. 5,192,678). The invention provides compositions containing crude or partially-purified *P. diminuta* BS-203 glutaryl 7-ACA amidase, and also provides isolated and purified *P. diminuta* BS-203 glutaryl 7-ACA amidase.

The glutaryl 7-ACA amidase of the invention is capable of catalyzing the hydrolysis of glutaryl 7-ACA into 7-ACA. It is composed of a 42,000 dalton large subunit and a 26,000 dalton small subunit. Cleavage of the precursor protein (SEQ ID NO:2) into subunits most probably occurs at the site indicated in FIG. 5, in view of the cleavage of the SE83 acyI cephalosporin acylase at the homologous position (Matsuda et al., *J. Bact.* 1987 169:5821–5826).

The glutaryl 7-ACA amidase of the invention is characterized by its ease of attachment to polyethyleneimine (PEI), which accordingly may be used in enzyme purification and immobilization processes as described further below.

The invention also relates to proteins which are at least 80% homologous to SEQ ID NO:2 or to a portion thereof, which are anticipated to have similar enzymatic activity so long as the enzyme active site is not substantially altered.

The glutaryl 7-ACA amidase of the invention was isolated and purified from a bacterial strain obtained from the soil designated BS-203. The BS-203 bacterium, which contains significant amidase activity against glutaryl 7-ACA, appears to belong to species *diminuta* of the *Pseudomonas* genus. Additional characteristics of the BS-203 strain are described in Example 1.

The invention also relates to isolated and purified nucleic acids encoding the glutaryl 7-ACA amidase of the invention, such as nucleic acids having the nucleotide sequence of SEQ ID NO:1, as well as fragments (or partial sequences) thereof. The invention also relates to nucleic acids which encode proteins which are at least 80% homologous to SEQ ID NO:2 and which have glutaryl 7-ACA amidase activity.

The invention also relates to nucleic acids having complementary (or antisense) sequences of the sequence shown in SEQ ID NO:1, preferably completely complementary sequences, as well as fragments (or partial sequences) thereof. Polynucleotides having partial sequences may be obtained by various methods, including restriction digestion of the complete nucleotide sequence of the glutaryl 7-ACA amidase gene, PCR amplification, and direct synthesis.

The invention provides nucleic acid molecules of between 10 and 1722 nucleotides, preferably between 17 and 1722 nucleotides, and most preferably between 20 and 1722 nucleotides, which hybridize to a DNA molecule having SEQ ID NO:1 or to a DNA molecule consisting of the complement of SEQ ID NO:1. Most preferably, such nucleic acid molecules hybridize to SEQ ID NO:1 or its complement when hybridization is conducted under stringent conditions, which are identical or equivalent to 4× SSPE, 10% PEG 6000, 0.5% SDS, 5× Denhardt's, and 50 µg/ml denatured salmon sperm DNA, buffered at 42° C. for 72 hours. Preferred fragments are those which are complementary to a portion of residues 293–1993 of SEQ ID NO:1, which is the coding region for the glutaryl 7-ACA protein. Particularly preferred are fragments which are at least 74% complimentary, more preferably 84% complimentary, and most preferably at least 94% complementary, to a portion of residues 293–1993 of SEQ ID NO:1. Probe #7 (SEQ ID NO:12), for example, was 94% complementary (16 matches out of 17 bases). The 77-base guess-mer probe (SEQ ID NO:22) was 74% complementary (57 matches), demonstrating the utility of probes having at least this level of homology.

Percent sequence identity with respect to the amino acid and nucleotide sequences identified herein is defined as the percentage of residues in one sequence that are identical with the residues in a second sequence, after aligning the sequences and introducing gaps, if necessary, to approach or achieve the maximum percent sequence identity. Conservative substitutions are not considered to contribute to sequence identity in amino acid sequences. Alignment for purposes of determining percent sequence identity can be achieved in various ways that are within the skill in the art, for instance, using publicly available computer software such as BLAST (S. Altschul et al., *Nucleic Acids Res.,* 1997, 25:3389–3402) or ALIGN (E. Myers and W. Miller, 1989, *CABIOS* 4:11–17). Those skilled in the art can determine appropriate parameters and algorithms needed to achieve maximal alignment over the full length of the sequences being compared.

The degree of homology or complementarity of short sequences can be readily determined by inspection, or for longer sequences by using the BLAST or ALIGN software. For example, the latter program (version 2.0u) was used with the BLOSUM50 scoring matrix and end-gap weighting, using a Smith-Waterman gap opening penalty of −16 and gap extension penalty of −4, to compare SEQ ID NO:1 to known 7-ACA amidase genes. With a gap opening penalty of −12 and a gap extension penalty of −2, the same program was used to compare the corresponding amino acid sequences.

The nucleotide sequences described herein represent only one embodiment of the present invention. Due to the degeneracy of the genetic code, it will be understood that numerous choices of nucleotides can be made that will lead to a sequence capable of directing production of the glutaryl 7-ACA amidases of the invention, or the subunits or peptide fragments thereof. As such, nucleic acid sequences which are functionally equivalent to the sequences described herein are intended to be encompassed within the present invention. Such sequences may be arrived at, for example, by substituting codons which are used preferentially by the host organism. The nucleic acids of the invention may also be isolated and substantially purified, by methods known in the art.

The nucleic acids of the invention may be present in vectors and/or in cultured host cells. The present invention therefore also relates to vectors and host cells comprising the nucleic acids of the invention.

The invention provides methods of obtaining compositions having glutaryl 7-ACA amidase activity, by culturing *Pseudomonas diminuta* BS-203 in a suitable medium, under conditions suitable for expression of the glutaryl 7-ACA amidase, and optionally recovering a protein fraction having the amidase activity. The invention also relates to methods of using the nucleic acids, vectors, and host cells of the invention to produce the glutaryl 7-ACA amidase of the invention. The invention further relates to a process for obtaining 7-aminocephalosporanic acid (7-ACA) or desacetyl 7-ACA from 7-β-(4-carboxybutanamido)-cephalosporanic acid (glutaryl 7-ACA) or desacetyl 7-β-(4-carboxybutanamido)-cephalosporanic acid by contacting such substrates with a glutaryl 7-ACA amidase of the invention.

The glutaryl 7-ACA amidases of the invention can be prepared by culturing a host cell transformed with an expression vector comprising a DNA sequence encoding the amino acid sequence of the enzyme, for example a DNA sequence encoding SEQ ID NO:2. The host cells may be cultured in a nutrient medium and the 7-ACA amidase may be subsequently recovered from the cells and/or medium. The host cells contemplated for use in the present invention can be microorganisms, yeast, fungi, plant, insect, or animal cell lines. In general, any host capable of expressing the glutaryl 7-ACA amidase enzyme in active form will be usable.

Suitable host cells include microorganisms (e.g. *Escherichia coli, Bacillus subtilis, Saccharomyces cerevisiae*), animal cell lines and cultured plant cells. Preferred microorganisms are bacteria, most preferably strains belonging to the genus *Escherichia* (e.g. *E. coli* JM109 ATCC 53323; *E. coli* HB101, ATCC 33694; *E. coli* HB101–16, FERM BP-1872; *E. coli* 294, ATCC 31446), or the genus *Bacillus* (e.g. *Bacillus subtilis* ISW1214). Preferable yeast hosts include strains belonging to the genus *Saccharomyces* (e.g. *Saccharomyces cerevisiae* AH22). Suitable animal cell lines include mouse L929 cells, Chinese hamster ovary (CHO) cells, and the like. Examples of suitable insect cells are those derived from *Spodoptera* (e.g., Sf9, Sf21), *Tricholplusia* (e.g. High Five™, Tn), *Drosophila*, and *Heliothis*. When bacteria are used as host cells, the expression vector is usually composed of at least a promoter, an initiation codon, a DNA sequence encoding SEQ ID NO:2 (or a portion thereof), a stop codon, terminator region, and a replication unit. When yeast or animal cells are used as host cells, the expression vector may include an enhancer sequence, splicing junctions, and a polyadenylation site.

The promoter for expression in bacteria usually comprises a Shine-Dalgarno sequence. Preferred promoters for bacterial expression are commercially available, conventionally employed promoters, such as the PL-promoter and trp-promoter for *E. coli*. Suitable promoters for expression in yeast include the promoter of the TRP1 gene, the ADHI or ADHII genes, and the acid phosphatase (PH05) gene for *S. cerevisiae*. The promoter for expression in mammalian cells may include SV40 early or late-promoter, HTLV-LTR-promoter, mouse metallothionein I (MMT) promoter, vaccinia promoter, and the like. Numerous other suitable promoters are known to those of skill in the art.

The vectors contemplated for use in the present invention include any vectors into which a nucleic acid sequence as described above can be inserted, along with any preferred or required operational elements, and which vector can then be subsequently transferred into a host cell and, preferably, replicated in such cell. Preferred vectors are those whose restriction sites have been well documented and which contain the operational elements preferred or required for transcription of the nucleic acid sequence. Vectors may also be used to prepare large amounts of nucleic acids of the invention, which may be used, e.g., to prepare probes or other nucleic acid constructs. Such probes may be used to identify homologous glutaryl 7-ACA amidase enzymes from other bacterial species.

The vectors of this invention may function in bacterial and/or eukaryotic cells. Suitable plasmids include plasmid pBR322 or modifications thereof for *E. coli*, yeast 2 μ plasmid or yeast chromosomal DNA for yeast, plasmid pRSVneo ATCC 37198, plasmid pSV2dhfr ATCC 37145, plasmid pdBPV-MMTneo ATCC 37224, and plasmid pSV2neo ATCC 37149 for mammalian cells. For mammalian cells, the enhancer sequence, polyadenylation site, and splicing junction may be derived from SV40. The vectors may optionally encode a cleavable signal peptide to enhance secretion.

The promoter, initiation codon, DNA encoding sequence, termination codon(s) and terminator region, and additional sequences appropriate to the host cell, can be incorporated into an appropriate replication unit (e.g., a plasmid), using e.g. linkers and restriction sites, in a conventional manner (e.g. digestion with restriction enzymes, ligation with T4 DNA ligase) to give an expression vector. Host cells can be transformed (transfected) with the expression vector by methods known in the art (e.g., calcium phosphate precipitation,, microinjection, electroporation, etc.)

The invention also relates to methods of using the nucleic acids of the invention to produce the glutaryl 7-ACA amidase of the invention. In one embodiment of the invention, the glutaryl 7-ACA amidase is prepared by a recombinant method which comprises:

a) preparing a nucleic acid capable of directing a host cell to produce the glutaryl 7-ACA amidase of the invention;

b) cloning the nucleic acid into a vector capable of being transferred into and replicated in a host cell, such vector containing operational elements for expressing the nucleic acid, if necessary;

c) transferring the vector containing the nucleic acid and operational elements into a host cell capable of expressing the glutaryl 7-ACA amidase;

d) growing the host under conditions appropriate for expression of the glutaryl 7-ACA amidase; and e) isolating the glutaryl 7-ACA amidase.

In another embodiment, the glutaryl 7-ACA amidase of the invention is isolated from a culture of *Pseudomonas diminuta*. An example of a method for isolating glutaryl 7-ACA amidase from *P. diminuta* is described in the Examples below.

The invention further relates to a process for obtaining 7-aminocephalosporanic acid (7-ACA) from a 7-β-(4-acylamido)cephalosporanic acid (e.g., glutaryl 7-ACA) using a glutaryl 7-ACA amidase of the invention. The process is carried out by treating glutaryl 7-ACA, or an equivalent acyl 7-ACA substrate, with a glutaryl 7-ACA amidase of the invention under conditions that permit hydrolysis of the acyl 7-ACA to 7-ACA. The glutaryl 7-ACA amidases of the invention may be employed in solution, or may be immobilized by cross-linking or by attachment to or entrapment in an insoluble support, by methods known in the art. See for example Cambiaghi et al., U.S. Pat. No. 5,424,196; J. Woodward, U.S. Pat. No. 5,846,762; M. Bigwood, U.S. Pat. No. 4,612,288; and M. Navia, U.S. Pat. No. 5,618,710, all of which are incorporated herein by reference.

The glutaryl 7-ACA amidases of the invention may be secreted into the culture medium by the host cells. In these embodiments, the enzyme is readily isolated by the usual methods if desired. Representative compositions of the invention which are useful for preparing 7-ACA are the culture broth itself, and concentrates, precipitates, and peptide fractions derived therefrom which contain the glutaryl 7-ACA amidase activity. If the expressed 7-ACA amidase remains within the host cells, the following compositions are representative embodiments of the invention:

(1) host cells; separated from the culture broth in a conventional manner such as filtration or centrifugation;

(2) dried cells; obtained by drying the above host cells in a conventional manners;

(3) cell-free extract; obtained by destroying the above host cells in a conventional manner (e.g., lysis with an organic solvent, homogenization, grinding, or ultrasonic irradiation) and optionally removing debris by filtration or centrifugation;

(4) precipitated enzyme, obtained by treating the above cell-free extract with a precipitant (e.g., sodium sulfate, trichloroacetic acid, poly(ethyleneimine), etc.)
(5) enzyme solution; obtained by purification or partial purification of the above cell-free extract in a conventional manner (e.g., ion exchange or hydrophobic interaction chromatography);
(6) immobilized cells or enzyme; prepared by immobilizing host cells or enzyme in a conventional manner (e.g., attachment to or entrapment within a polymer, attachment to a particulate support, crosslinking, etc.).

The process of contacting the glutaryl 7-ACA amidase of the invention with glutaryl 7-ACA may be conducted in any suitable solvent, i.e. a solvent in which the substrate is soluble and in which the enzyme is active. The solvent is preferably an aqueous medium such as water or a buffer solution. Typically the process is carried out by dissolving or suspending the culture broth or one of the above representative compositions in a buffer solution containing glutaryl 7-ACA or an equivalent substrate. The pH of the reaction mixture, concentration of the substrate, reaction time and reaction temperature may vary with properties of a cultured broth or its processed material to be used. Preferably the reaction is carried out at pH between 6 and 10, more preferably between pH 7 and 9; and preferably between 0° C. and 40° C., more preferably between 4° C. and 15° C., for 0.5 to 5.0 hours. The concentration of the substrate in the reaction mixture is preferably between 1 and 100 mg/ml. The produced 7-ACA can be purified and isolated from the reaction mixture by the methods known in the art.

It is expected that, like previously known glutaryl 7-ACA amidases, the enzymes of the present invention will be capable of hydrolysis of other acyl 7-ACA substrates, such as for example succinyl 7-ACA and malonyl 7-ACA, and thus will be useful for the conversion of such alternative and equivalent substrates into 7-ACA. The term 7-β-(acylamido)-cephalosporanic acid refers to 7-ACA derivatives known to be substrates for other cephalosporin amidases and acylases (E.C. 3.5.1.11). In general, this class consists of compounds where acylamido is a carboxy-substituted acylamido group of three to six carbons; more specifically it includes compounds where acylamido is selected from the group consisting of malonylamido, succinylamido, glutarylamido, and 5-carboxy-5-oxopentanamido.

The enzymes of the present invention are also capable of hydrolysis of the desacetyl derivatives of glutaryl 7-ACA and other 7-β-(acylamido)-cephalosporanic acids, thereby producing desacetyl 7-ACA. The invention accordingly also provides methods of producing desacetyl 7-ACA from these derivatives.

The present invention will now be described by way of examples, which are meant to illustrate, but not limit, the scope of the invention.

EXAMPLES

Example 1

Identification of Strain BS-203

The bacterium designated BS-203 was isolated from soil during the course of an investigation of microorganisms with glutaryl 7-ACA amidase activity. The bacterium has been deposited under the provisions of the Budapest Treaty with the American Type Culture Collection, with ATCC reference No. PTA-2517.

This bacterium, which contained significant amidase activity against glutaryl cephalosporanic acid, had the following characteristics:

A. Morphology

The bacterium is a strictly aerobic, Gram-negative, non-sporulating, motile rod. It measures $0.5-0.8 \times 2-4$ μm with rounded ends and a single polar flagellum.

B. Cultural and Physiological Characteristics

Colonies on a nutrient agar are circular, convex, smooth and colorless. Glucose is metabolized oxidatively, and indole production is negative. Growth is observed at 20° C. and 28° C., but not at 5° C. or 37° C. Furthermore, the strain fails to grow in synthetic media, suggesting a growth factor requirement (Table 1). When synthetic media are supplemented with yeast extract, the strain grows well. The physiological properties are summarized in Table 2.

TABLE 1

Growth of Strain BS-203 on Various Media

| Media | Growth |
|---|---|
| Yeast Extract - Malt extract agar | + |
| Oatmeal agar | − |
| Inorganic salts - starch agar | − |
| Glycerol - asparagine agar | − |
| Peptone - yeast extract - iron agar | + |
| Tyrosine agar | − |
| Czapek agar | − |
| Glucose - asparagine agar | − |
| V-8 juice agar | + |

TABLE 2

Physiological properties of strain BS-203

| | |
|---|---|
| Catalase reaction | + |
| Oxidase reaction | + |
| Indole production | − |
| OF test | Oxidative |
| Growth temperature | 15 to 30° C. |
| Formation of fluorescent pigments | − |
| Accumulation of Polyhydroxybutyrate | − |
| Arginine dihydrolase | − |
| Denitrification | − |
| Starch Hydrolysis | − |
| Growth factor | Required |
| Fixation of atmospheric nitrogen | − |
| Halophilic nature | − |
| Growth at extreme pH (e.g. pH 3.5) | − |
| Oxidation of ethanol or methanol | − |
| Anaerobic nature | − |

TABLE 3

Comparison of BS-203 with related *Pseudomonas* species

| | BS-203 | P. Diminuta | P. Vesicularis | P. Iners |
|---|---|---|---|---|
| Colonies, yellow | − | − | + | − |
| Number of flagella | 1 | 1 | 1 | 1 |
| Oxidase reaction | + | + | + | − |
| Starch Hydrolysis | − | | | − |
| Denitrification | − | − | − | − |
| Accumulation of PHB | − | + | + | |
| Growth factor requirements | Complex Media (Table 1) | Pantothenate Biotin Vitamin $B_{12}$ Methionine | Pantothenate Biotin Vitamin $B_{12}$ | ? |

C. Taxonomic Position

The taxonomic features of strain BS-203 indicate that the strain can be placed in the genus *Pseudomonas* (N. Palleroni, *Family I. Pseudomonadeaceae*, pp. 141–199, in N. Krieg (ed.) *Bergey's Manual of Systematic Bacteriology*, 9th ed., vol. 1 (1986), Williams & Wilkins, Baltimore; H. Stolp and D. Gadkari, *Nonpathogenic members of the genus Pseudomonas*, pp. 719–741, in M. P. Starr et al. (eds.) *The Prokaryotes: a handbook on habitats, isolation and identification of bacteria* vol. I (1981), Springer-Verlag, Berlin.) Strain BS-203 seems to be closely related to the group *P. diminuta*, which require specific growth factors (Palleroni, supra, p. 184) (Table 3).

Example 2

Isolation and Purification of Active Glutaryl Cephalosporin Amidase

BS-203 was grown in 500 liters of medium containing 1% casein hydrolysate (NZAmine A, Sheffield), 1% yeast extract (Amberex 1003), 1% casein hydrolysate (CER90C, Deltown) pH 7.0 at 28° C. using 0.2 VVM air flow at 5 PSIG with vigorous agitation. After 44 hour growth, 1 Kg of cells were harvested by centrifugation.

The cells were resuspended in 2.5 liters of water and homogenized using a TISSUEMIZER™ brand homogenizer (Tekmar) operating at maximum speed. The viscosity of the homogenate was controlled by adding 100 mg of DNAse (Sigma). Cell debris was removed by centrifugation (7000×g for 20 min) in the presence of 0.1% poly (ethyleneimine). An additional 0.3% poly(ethyleneimine) was added, and the precipitating glutaryl 7-ACA amidase activity was removed by an additional centrifugation.

The active amidase was resuspended by dissolving the pellet in 80 ml of a 0.6 M NaCl, 20 mM Tris buffer (pH 8.0) solution. This suspension was diluted three-fold with water and centrifuged to clarify the solution. The clear supernatant was loaded onto a 40 ml Q-Sepharose ion-exchange column equilibrated with 0.15 M NaCl, 50 mM Tris-Cl (pH 8.5). The activity was eluted using a 0.15 to 0.75 M NaCl salt gradient. Peak active fractions eluting near 300 mM NaCl were pooled, concentrated and loaded onto a S-200 size-exclusion column. The column was eluted with 0.25 M NaCl, 0.05 M Tris-Cl (pH 8). Fractions containing glutaryl 7-ACA amidase activity were pooled, dialysed against 10 mM potassium phosphate buffer and loaded onto a 13 ml column of hydroxyapatite (Biorad HTP). The amidase was eluted with a potassium phosphate gradient (10 to 600 mM). Fractions containing peak amidase activity were pooled and loaded on to a DEAE Trisacryl™ ion exchange column equilibrated in 30 mM Tris-Cl (pH 8.4). This polishing column was eluted with a salt gradient (0 to 600 mM) containing 30 mM Tris-HCl. The peak fractions eluting from this column still contained significant amounts of contaminating proteins, so further purification was done using preparative native gel electrophoresis according to the method of Davis (Davis, *Ann. N.Y. Acad. Sci.*, 1964, 121:404–427).

Native gel electrophoresis of the semi-purified amidase from the second DEAE-Trisacryl column separated contaminating proteins from the amidase. Identity was confirmed by activity assay of protein eluted from slices of the native gel; homogeneity was confirmed by both native and SDS gel electrophoresis of the eluted protein. A preparative SDS gel electrophoresis was run on the eluted native amidase from the native gel to separate the two subunits of this protein. Both the large unit, which has a molecular weight of 42,000 daltons, and the small subunit, which has a molecular weight of 26,000 daltons, were eluted from the preparative SDS gel, dialysed and concentrated. These preparations were digested with trypsin, and isolated fragments used to determine N-terminal amino acid sequences of fragments from the two subunits. These amino acid sequences are shown in FIGS. 2 and 3.

Example 3

Isolation of the Gene Encoding Glutaryl Cephalosporin Amidase from BS-203

A. Preparation of Chromosomal DNA from BS-203

100 ml of Luria Bertani (LB) media was inoculated with 1 ml of a confluent culture of BS-203. The culture was shaken at 28° C. for 24 hours at 200 rpm. The cells were pelleted for 15 minutes in a TJ-6 Beckman table-top centrifuge at 6000 rpm's. The cells were resuspended in 4 ml of 50 mM glucose/10 mM EDTA/25 mM Tris-HCl pH 8.0 and incubated with 10 mg of powered lysozyme (Sigma) for 15 minutes at 37° C. The cells were lysed by adding 1 ml of 2% sodium dodecyl sulfate (SDS) and 50 µg/ml proteinase K at 50° C. for 3 hours. The suspension was successively extracted with 1 ml of phenol, 1 ml of chloroform and 1 ml of ether. It was then precipitated by adding 30 µl of 5M NaCl, 2 ml of 100% ethanol and gently mixed by inversion until a clot was formed. The DNA clot was removed using a sealed, hooked Pasteur pipette and then successively rinsed in 70%, 85% and 100% ethanol solutions. The 70% and 85% ethanol solutions were diluted with 10 mM Tris pH8.0, 10 mM EDTA and 150 mM NaCl. The DNA was allowed to dissolve in 0.5 ml TE (10 mM Tris-HCl pH 8.0, 1 mM EDTA pH 8.0) at 22° C. for 16 hours. RNase A was added to 50 µg/ml and incubated at 37° C. for 2 hours, followed by a second digestion in 0.5% SDS and 50 µg/ml proteinase K at 37° C. for 16 hours. The organic extractions and ethanol precipitation were repeated. The final DNA clot was dissolved in 0.4 ml TE. The DNA concentration was determined spectrophotometrically at 260 nm.

B. Construction of Genomic Cosmid DNA Library of BS-203

Figure 6:
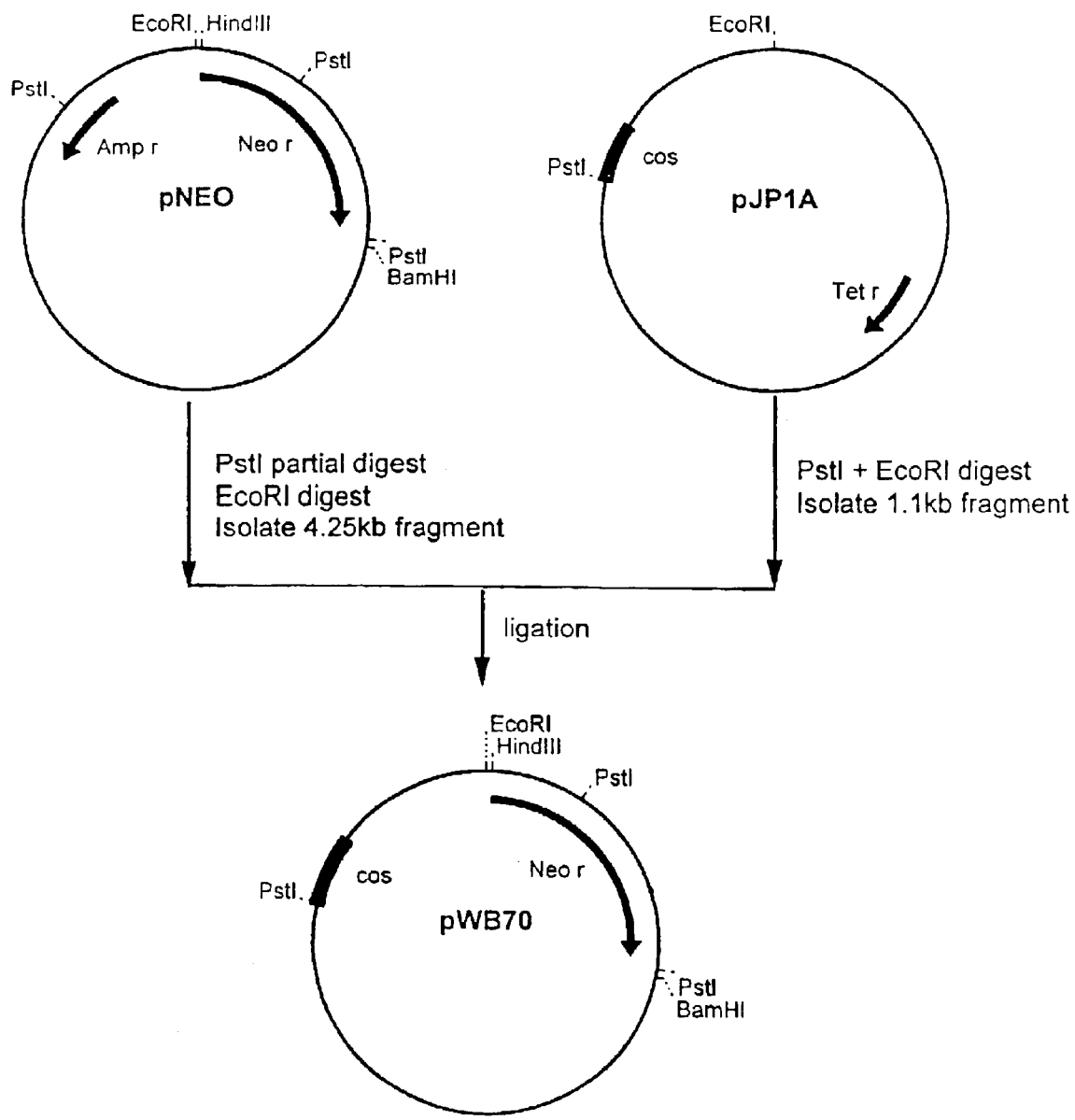
FIG. 6 shows the method of construction of the plasmid pWB70. Abbreviations used: cos is the bacteriophage lambda cohesive end; Neo r, Amp r, and Tet r are genes encoding resistance to neomycin, ampicillin, and tetracycline, respectively.

To generate a genomic cosmid library from BS-203, a new cosmid vector, pWB70, was used. The vector was constructed from the plasmids pNEO (R. A. Jorgensen et al., *Mol. Gene Genet.* 177:65–72 (1979)) and pJP1A (J. J. Portmore et al., *Biotech. Letters* 9:7–12 (1987)), as shown in FIG. 6. The plasmid pNEO was partially digested with Pst I and completely digested with Eco RI. A 4.2 kilobase (Kb) fragment was isolated by preparative agarose gel electrophoresis and purified using Geneclean™ (BIO 101). pJP1A was digested with Pst I and Eco RI and a 1.1 Kb fragment containing the cos site of bacteriophage lambda, which allows DNA to be packaged into lambda phage heads, was isolated. The two fragments were ligated, and the transformants were screened for neomycin resistance and ampicillin sensitivity. This vector, which produces no β-lactamase activity and confers resistance to neomycin, allows large (30–45 Kb) chromosomal DNA fragments to be inserted into *E. coli*, generating a genomic cosmid library.

The following method was used to generate a genomic cosmid library from BS-203: Cosmid pWB70 was digested with Bam HI and dephosphorylated with bacterial alkaline phosphatase (BAP) to prevent self-ligation. To establish optimal conditions to generate DNA fragments between 30–45 Kb necessary for cosmid cloning, BS-203 high molecular weight chromosomal DNA was digested with various amounts of Sau 3AI for one hour at 37° C. Sau 3AI recognizes the 4 base pair (bp) sequence GATC and generates a cohesive end that can be ligated to a Bam HI cohesive end. An enzyme concentration of 0.016 units/µg of DNA gave the greatest concentration of DNA fragments in the 30–45 Kb range. These conditions were used to prepare a large amount of partially digested BS-203 DNA. The DNA was fractionated through a 10–40% sucrose gradient in order to enrich for DNA fragments between 30–45 Kb. Fractions (0.4 ml) were collected and every third fraction was analyzed by electrophoresis through a 0.4% agarose gel. Fractions containing the proper size fragments were pooled and ethanol precipitated twice. Final analysis by agarose gel electrophoresis indicated that the DNA was the correct size for cosmid cloning.

The enriched BS-203 DNA fragments (30–45 Kb) were ligated to Bam HI digested pWB70 with T4 DNA ligase (BRL) at 22° C. for 16 hours. Following the manufacturer instructions, the ligation mix was packaged in vitro using the Gigapack II Gold™ kit (Stratagene). The transfectants were selected on LB agar containing 30 µg/ml neomycin. The packaging efficiency was about $7.2 \times 10^3$ transfectants/µg of insert DNA.

Colony blots of the BS-203 genomic cosmid library were prepared to screen for the glutaryl 7-ACA amidase gene. Transfectants were transferred to an 82 mm, 0.45 µm nitrocellulose filter (Schleicher & Schuell). The transfectants were then amplified by transferring the filter to an LB agar plate containing 170 µg/ml chloramphenicol and incubated at 37° C. for 16 hours. The DNA was bound to the filter by transferring the filter (colony side up) to 3MM paper saturated with the following solutions: 10% SDS for 3 minutes, 0.5M NaOH/1.5M NaCl for 5 minutes, 1.5M NaCl/0.5M Tris-Cl pH 7.5 for 5 minutes and 2× SSPE for 5 minutes. The filter was air dried for 30 minutes and then baked at 80° C. for 30 minutes in a vacuum oven. To remove bacterial debris, the filter was incubated in 1× SSPE/0.5% SDS/50 µg/ml proteinase K for 30 minutes at 42° C. The bacterial debris was removed by gently rubbing the filter with a gloved finger in 2× SSPE/0.1% SDS preheated to 65° C. The filter was then washed twice in 2× SSPE for 5 minutes each, air dried and covered until hybridization.

C. Selection of Clones Containing the Glutaryl Cephalosporin Amidase Gene

Sixteen 17-mer degenerate oligonucleotide probes, derived from the amino acid sequence of glutaryl 7-ACA amidase, were synthesized with an Applied Biosystems 391 DNA Synthesizer PCR-MATE™ (FIG. 2), end-labeled with [γ-$^{32}$P]ATP (Amersham), and used to probe a Southern blot (Southern, E. M. 1975, *J. Mol. Biol.* 98:503–517) of BS-203 chromosomal DNA digested with restriction endonucleases HindIII and Pst I. Hybridization was conducted in 4× SSPE, 10% PEG 6000, 0.5% SDS, 5× Denhardt's (0.1% Ficoll, 0.1% polyvinylpyrroidone, 0.1% bovine serum albumin) and 50 µg/ml denatured salmon sperm DNA buffer at 42° C. for 72 hours. Hybridization wash conditions were as follows: twice in 5× SSPE/ 0.1% SDS at 20–25° C. (room temperature) for five minutes each, twice in 5× SSPE/0.1% SDS at 45° C. for five minutes each, and twice in 5× SSPE at 20–25° C. for five minutes each. Nine of the probes hybridized to the Southern blots. Of these nine probes, four were selected to screen colony blots of the genomic cosmid library. Each probe was used to screen four colony blots containing about 200 transfectants each, using the same hybridization and washing conditions as above except that the hybridization time was shortened to 48 hours. Twelve transfectants identified with probe #3 (SEQ ID NO:8) and probe #7 (SEQ ID NO:12) were selected. for further evaluation. Plasmid DNA was isolated from each transfectant using the TELT mini-prep method (He et al., 1990, *Nucl. Acids Res.*, 18:1660). Southern analysis of these clones identified five cosmid clones that hybridized to both the 17-mer oligonucleotide probes and a 77 base guess-mer probe (Lathe, R., 1985, *J. Mol. Biol.* 183:1–12). The 77 base guess-mer probe (FIG. 3) was designed and synthesized based upon the amino acid sequence described in FIG. 2. Hybridization was conducted in 2× SSC, 5× Denhardt's, 0.5% SDS and 100 µg/ml denatured salmon sperm DNA buffer at 50° C. for 48 hours. Hybridization wash conditions were as follows: twice in 2× SSC/0.5% SDS at 20–25° C. for ten minutes each, once in 2× SSC/0.5% SDS at 60° C. for twenty minutes, and once in 2× SSC at 20–25° C. for five minutes. These five cosmid clones were further evaluated for glutaryl 7-ACA amidase activity. Three showed a significant amount of activity, and clone 7.10 showed the most.

Due to its convenient size, a 2.3 Kb Pst I fragment from cosmid clone 7.10 that had hybridized to the oligonucleotide probe was isolated and subcloned into the bacteriophage M13mp vector that had been cleaved with Pst I and dephosphorylated with BAP. Nucleotide sequencing of the 2.3 Kb Pst I fragment from cosmid clone 7.10 identified the sequences complimentary to the 17-mer and 77 base guess-mer probes used to identify the gene. Translation of the adjacent DNA sequence produced an amino acid sequence that was identical to the previously determined amino acid sequences (FIGS. 2 and 3).

Translation of the nucleotide sequence of the entire 2.3 Kb Pst I fragment revealed that the 3'-end of the glutaryl 7-ACA amidase gene was missing. Therefore, the 3'-end had to be subcloned in order to sequence the 3'-end of the gene and to reconstruct the full-length gene. Sequencing had identified a Hind III site about 100 base pairs upstream of the translation start site. Therefore, an 11 Kb Hind III fragment from cosmid clone 7.10 that had hybridized to both the 17-mer oligonucleotide probe and the 77 base guess-mer probe was isolated and subcloned into pUC19 that had been cleaved with Hind III. Transformants were screened and one was chosen for further evaluation. To trim the 3'-end non-coding region of this clone containing the 11 Kb Hind III fragment, the clone was digested to completion with Bam HI and then partially digested with Sau 3AI. Aliquots were taken at 5, 10 and 20 minutes, combined and electrophoresed through an agarose preparative gel. A 4.8–5.8 Kb range was excised from the gel and isolated. The 4.8–5.8 Kb fragment was re-ligated to itself and used to transform DH5α cells. Miniprep DNA was prepared from 12 transformants and screened by EcoRI digests. Clone #6 contained a 1.8 Kb EcoRI fragment, which contains additional 1000 bases of sequence downstream from the Pst I site. This fragment was isolated, cloned into M13mp19 and used to sequence the 3'-end of the gene.

D. Determination of Nucleotide Sequence

The nucleotide sequence of the glutaryl 7-ACA amidase gene encoded on the 2.3 Kb Pst I and the 1.8 Kb EcoRI fragments was determined by the dideoxy chain termination method (Sanger et al. 1977, *Proc. Natl. Acad. Sci. U.S.A.* 74:5463–5467) using the TAQ TRACK™ sequencing system (Promega). Two clones were identified containing the 2.3 Kb Pst I fragment in opposite orientation. A set of unidirectional, nested deletions from one end of the insert was generated using exonuclease III. Single-stranded DNA (M13 Cloning/Dideoxy Sequencing Instruction Manual, Bethesda Research Laboratories Life Technologies, Inc., form #19541:44–49) was isolated from the deletions and used for sequencing. Single-stranded DNA was also isolated from the 1.8 Kb EcoRI fragment cloned into M13mp19 and used to sequence the 3'-end of the gene. The M13 (−20) primer 5'-GTAAAACGACGGCCAGT-3' (SEQ ID NO:23) (Stratagene) and synthesized internal primers were used to sequence the entire gene from both strands. Electrophoresis was performed on an 8% polyacrylamide gel containing 8M urea in TBE (0.089M Tris-borate, 0.089M boric acid, 0.002M EDTA) buffer and a 5% HYDROLINK LONG RANGER™ (FMC BioProducts, U.S.A) polyacrylamide gel containing 7M urea in TBE buffer at 2700 volts.

The complete nucleotide sequence is shown in FIG. 4. The coding region is 1701 bp long and codes for a 567 amino acid protein (MW=60 kD). The sequences complimentary to the 17-mer and 77-base guess-mer probes used to identify the gene are underlined in FIG. 4.

The protein sequence (SEQ ID NO:2) determined from the translation of the DNA sequence contains amino acid sequences identical to the amino acid sequences identified in FIGS. 2 and 3.

Example 4

Glutaryl 7-ACA Amidase Sub-cloning and Expression in E. coli

In order to facilitate the sub-cloning of the glutaryl 7-ACA amidase gene into plasmid vectors for enzyme expression in E. coli, oligonucleotide-directed site-specific mutagenesis was performed on the genomic clone of glutaryl 7-ACA amidase in order to introduce a restriction enzyme site at the translation initiation codon (ATG) of the gene, utilizing the method of Morinaga (Morinaga et. al., 1984, Bio/Technology 7:636–639). The synthetic oligonucleotide mutagen containing a single base change (A to T) giving rise to a BspHI site (TCATGA) is illustrated below:

```
a) glutaryl 7-ACA amidase sequence
to be mutagenized:
5' ....TTGAGATCCGACATGACCCGT.... 3'   (SEQ ID NO:24)

b) synthetic oligonucleotide
(21 mer):
5'     TTGAGATCCGTCATGACCCGT       3'  (SEQ ID NO:25)
```

Successfully mutagenized glutaryl 7-ACA amidase DNA was identified by cleavage with restriction enzyme BspHI, and confirmed by DNA sequence analysis. The glutaryl 7-ACA amidase gene was then isolated from the genomic clone plasmid by digestion with restriction enzymes BspHI and BamHI, ligated into E. coli expression plasmid pBMS2000 (FIG. 1), and transformed into E. coli strain BL21. Recombinant cultures, selected on LB agar plates (1% Bacto tryptone, 0.5% NaCl, 0.5% yeast extract, and 1.5% agar, supplemented with 30 μg/ml neomycin) were grown in LB medium plus 30 μg/ml neomycin and induced during exponential growth with 60 μM isopropyl-β-D-thiogalactopyranoside (IPTG) for four hours. Lysates of IPTG-induced recombinant E. coli BL21 harboring plasmid pBMS2000/GCA successfully converted glutaryl 7-ACA to 7-aminocephalosporanic acid, indicating active glutaryl 7-ACA amidase enzymatic activity (non-transformed BL21 has no glutaryl 7-ACA amidase activity). The same lysates subjected to SDS-PAGE (reduced) analysis revealed new protein bands of 26 and 42 kilodaltons (kd) corresponding to the small and large subunits of glutaryl 7-ACA amidase.

For larger scale production, a preferred fermentation process is as follows: The recombinant E. coli BL21 is cultured in a medium containing dipotassium phosphate 3 g/l; monopotassium phosphate 2 g/l; magnesium sulfate 2 g/l; yeast extract 3 g/l; ammonium sulfate 0.5 g/l; ferrous sulfate 0.03 g/l; and kanamycin 0.03 g/l. Fermentation is carried out at 30° C. with air flow at 1.0 VVM@7 PSIG; the pH is maintained at 7.0 with ammonia gas. The culture is fed a solution of 20% casein hydrolysate and 20% glucose so as to maintain a linear growth rate. Amidase production is induced with 150 μM IPTG after 10 hours of fermentation. The fermentation is halted when amidase titer reaches a maximum, usually at a cell density of approximately 40 grams per liter (cell dry weight) after approximately 45 hours. The whole broth is homogenized to release amidase and clarified by filtration.

For immobilization of the enzyme, a preferred method is to treat the active filtrate with 5% diatomaceous earth, 0.5% polyallylamine, and 0.2% polyethyleneimine. The mixture is then treated with 0.15% glutaraldehyde at pH 8.0 to immobilize the amidase upon the diatomaceous earth. The amidase can then be recovered by filtration.

The immobilized amidase may be used to convert glutaryl-7-ACA to 7-ACA by stirring an aqueous suspension at 4° C., with the pH maintained at 9.0 with ammonia, with a substrate concentration of 100 g/l glutaryl-7-ACA. The yield is approximately 90% with a 95% mass balance.

What is claimed is:

1. An isolated glutaryl 7-ACA amidase having the following characteristics: isolatable from *Pseudomonas diminuta* BS-203, catalyzes the hydrolysis of 7-β-(4-carboxybutanamido)-cephalosporanic acid to 7-aminocephalosporanic acid and glutaric acid, and is composed of two subunits having apparent molecular weights of 42 kd and 26 kd by SDS PAGE electrophoresis.

2. The isolated glutaryl 7-ACA amidase according to claim 1, wherein said amidase comprises the amino acid sequence shown in SEQ ID NO:2.

3. The isolated glutaryl 7-ACA amidase according to claim 1, wherein said amidase consists of the amino acid sequence shown in SEQ ID NO:2.

4. The isolated glutaryl 7-ACA amidase of claim 1, wherein the glutaryl 7-ACA amidase is immobilized on an insoluble support.

5. A method for preparing an isolated glutaryl 7-ACA amidase from *Pseudomonas diminuta* BS-203, said method comprising
   (a) culturing the *Pseudomonas diminuta* BS-203 bacterium under aerobic conditions in a suitable medium; and
   (b) recovering from the obtained culture a protein fraction having glutaryl 7-ACA amidase activity.

6. A process for obtaining 7-aminocephalosporanic acid from a 7-β-(acylamido)cephalosporanic acid, comprising contacting a 7-β-(acylamido)cephalosporanic acid with the glutaryl 7-ACA amidase according to claim 1 in a suitable solvent.

7. A process for obtaining 7-aminocephalosporanic acid from a 7-β-(acylamido)cephalosporanic acid, comprising contacting a 7-β-(acylamido)cephalosporanic acid with the glutaryl 7-ACA amidase according to claim 2 a suitable solvent.

8. A process for obtaining 7-aminocephalosporanic acid from a 7-β-(acylamido)cephalosporanic acid, comprising contacting a 7-β-(acylamido)cephalosporanic acid with the glutaryl 7-ACA amidase according to claim 3 in a suitable solvent.

9. A process for obtaining 7-aminocephalosporanic acid from a 7-β-(acylamido)cephalosporanic acid, comprising contacting a 7-β-(acylamido)cephalosporanic acid with the glutaryl 7-ACA amidase according to claim 4 in a suitable solvent.

10. The process of claim 6, wherein the 7-β-(acylamido) cephalosporanic acid is 7-β-(4-carboxybutanamido) cephalosporanic acid.

11. The process of claim 7, wherein the 7-β-(acylamido) cephalosporanic acid is 7-β-(4-carboxybutanamido) cephalosporanic acid.

12. The process of claim 8, wherein the 7-β-(acylamido) cephalosporanic acid is 7-β-(4-carboxybutanamido) cephalosporanic acid.

13. The process of claim 9, wherein the 7-β-(acylamido)cephalosporanic acid is 7-β-(4-carboxybutanamido)cephalosporanic acid.

14. A process for obtaining desacetyl 7-aminocephalosporanic acid from a desacetyl 7-β-(acylamido)cephalosporanic acid, comprising contacting a desacetyl 7-β-(acylamido)cephalosporanic acid with the glutaryl 7-ACA amidase according to claim 1 in a suitable solvent.

15. A process for obtaining desacetyl 7-aminocephalosporanic acid from a desacetyl 7-β-(acylamido)cephalosporanic acid, comprising contacting a desacetyl 7-β-(acylamido)cephalosporanic acid with the glutaryl 7-ACA amidase according to claim 2 in a suitable solvent.

16. A process for obtaining desacetyl 7-aminocephalosporanic acid from a desacetyl 7-β-(acylamido)cephalosporanic acid, comprising contacting a desacetyl 7-β-(acylamido)cephalosporanic acid with the glutaryl 7-ACA amidase according to claim 3 in a suitable solvent.

17. A process for obtaining desacetyl 7-aminocephalosporanic acid from a desacetyl 7-β-(acylamido)cephalosporanic acid, comprising contacting a desacetyl 7-β-(acylamido)cephalosporanic acid with the glutaryl 7-ACA amidase according to claim 4 in a suitable solvent.

18. The process of claim 14, wherein the desacetyl 7-β-(acylamido)cephalosporanic acid is desacetyl 7-β-(4-carboxybutanamido)cephalosporanic acid.

19. The process of claim 15, wherein the desacetyl 7-β-(acylamido)cephalosporanic acid is desacetyl 7-β-(4-carboxybutanamido)cephalosporanic acid.

20. The process of claim 16, wherein the desacetyl 7-β-(acylamido)cephalosporanic acid is desacetyl 7-β-(4-carboxybutanamido)cephalosporanic acid.

21. The process of claim 17, wherein the desacetyl 7-β-(acylamido)cephalosporanic acid is desacetyl 7-β-(4-carboxybutanamido)cephalosporanic acid.

* * * * *